United States Patent
Kullenberg et al.

(10) Patent No.: US 10,203,292 B2
(45) Date of Patent: Feb. 12, 2019

(54) METHOD AND APPARATUS FOR ESTIMATION OF HEAT VALUE

(75) Inventors: Ragnar Kullenberg, Oskarström (SE);
Fredrik Danielsson, Vasteras (SE);
Eric Landstrom, Stockholm (SE)

(73) Assignee: MANTEX AB, Kista (SE)

( * ) Notice: Subject to any disclaimer, the term of this patent is extended or adjusted under 35 U.S.C. 154(b) by 1214 days.

(21) Appl. No.: 14/128,299

(22) PCT Filed: Jun. 28, 2012

(86) PCT No.: PCT/EP2012/062596
§ 371 (c)(1),
(2), (4) Date: Mar. 18, 2014

(87) PCT Pub. No.: WO2013/004593
PCT Pub. Date: Jan. 10, 2013

(65) Prior Publication Data
US 2014/0226694 A1 Aug. 14, 2014

(30) Foreign Application Priority Data
Jul. 7, 2011 (EP) .................................. 11173046

(51) Int. Cl.
*G01N 25/22* (2006.01)
*G01N 23/087* (2018.01)
(Continued)

(52) U.S. Cl.
CPC ........... *G01N 25/22* (2013.01); *G01N 23/087* (2013.01); *G01N 33/22* (2013.01); *G01N 33/46* (2013.01); *G01N 2223/619* (2013.01)

(58) Field of Classification Search
CPC .................................................. G01N 25/22
See application file for complete search history.

(56) References Cited

U.S. PATENT DOCUMENTS

| 3,934,139 A | 1/1976 | Ohata et al. |
| 7,690,268 B2 | 4/2010 | Wolfschaffner |
| 2006/0092423 A1 | 5/2006 | Servaites et al. |

FOREIGN PATENT DOCUMENTS

| EP | 0 718 553 A1 | 6/1996 |
| WO | WO-99/34193 A1 | 7/1999 |

(Continued)

OTHER PUBLICATIONS

Nystrom et al., "Methods for determination of moisture content in woodchips for power plants—a review," FUEL 83 (2004) 773-779.*
(Continued)

*Primary Examiner* — John Breene
*Assistant Examiner* — Jeffrey C Morgan
(74) *Attorney, Agent, or Firm* — Harness, Dickey & Pierce, P.L.C.

(57) ABSTRACT

A method for estimating a heating value of a biological material is disclosed. The method comprises: correlating amounts of radiation transmitted through a number of different reference materials, said radiation being electromagnetic radiation of at least two energy levels, with heating values for said reference materials obtained by calorimeter measurements; irradiating the biological material (102) with electromagnetic radiation of said at least two different energy levels;and measuring the amount of radiation (109a-c) transmitted through said biological material at said energy levels. The method further comprises determining, for each energy level, a transmission value through the biological material based on the radiation through said biological material; and determining, based on said determined transmission values and said correlation, an estimate of the heating value of said biological material. A corresponding apparatus (100) is also disclosed.

24 Claims, 3 Drawing Sheets

(51) Int. Cl.
*G01N 33/22* (2006.01)
*G01N 33/46* (2006.01)

(56) References Cited

FOREIGN PATENT DOCUMENTS

| WO | WO-2010037820 A1 | 4/2010 |
| WO | WO-2011/092192 A1 | 8/2011 |

OTHER PUBLICATIONS

D4 Reference: C200 Bomb Calorimeter, 3 pages (2006).
Office Action issued by the Patent Office of Russian Federation for Application No. 2013156528/5 (088158) dated Apr. 27, 2016 with English transaction.
A manual of the device disclosed in the D4 reference titled "Calorimeter System C200" produced by IKA-WERKE GmbH & Co KG and found at: http://www.ika.com.my/images/Calorimeter/manual_c_200_e.pdf.
Huang et al: "Ultimate analysis and heating value prediction of straw by near infrared spectroscopy," Waste Management, Elsevier, New York, NY, US, vol. 29, No. 6, Jun. 1, 2009 (Jun. 1, 2009), pp. 1793-1797, XP026080845, ISSN: 0956-053X, DOI: 10.1016/J.WASMAN.2008.11.027.
Huang et al: "Prediction of heating value of straw by proximate data, and near infrared spectroscopy," Energy Conversion and Management, Elsevier Science Publishers, Oxford, GB, vol. 49, No. 12, Dec. 1, 2008 (Dec. 1, 2008), pp. 3433-3438, XP025571314, ISSN: 0196-8904, DOI: 10.1016/J.ENCONMAN.2008.08.020.
Raja Sekhar et al: "Gamma-ray transmission technique for quality control of coal seams," Canadian Journal of Physics, NRC Research Press, CA, vol. 80, Jan. 1, 2002 (Jan. 1, 2002), pp. 551-555, XP009153764, ISSN: 0008-4204, DOI: 10.1139/P01-145.
Raja Sekhar et. al: "Rapid quality control for coal seams by gamma ray transmission technique," Applied Radiation and Isotopes, Elsevier, Oxford, GB, vol. 51, No. 3, Sep. 1, 1999 (Sep. 1, 1999), pp. 269-272, XP004167606, ISSN: 0969-8043, DOI: 10.1016/S0969-8043(99)00043-3.
International Search Report for PCT/EP2012/062596, dated Nov. 16, 2012; ISA/EP.
NIRS—Getting started; US Dairy Forage Research Center; 2004 Consortium Annual Meeting, 31 pages.

\* cited by examiner

METHOD AND APPARATUS FOR ESTIMATION OF HEAT VALUE

CROSS-REFERENCE TO RELATED APPLICATIONS

This application is a 371 U.S. National Stage of International Application No. PCT/EP2012/062596, filed on Jun. 28, 2012, which claims priority to European Patent Application No. 11173046.1, filed Jul. 7, 2011, the contents of which are hereby incorporated by reference in their entirety as if fully set forth herein.

TECHNICAL FIELD OF THE INVENTION

The present invention relates to a method and an apparatus for estimation of the heat value of a biological material in an automated procedure. The invention is particularly useful for measuring the heating value of biofuels, such as wood chips and coal.

BACKGROUND

Biological materials, and in particular biomass fuels, are commonly used in burn processes for generation of heat and energy. One of the most important biomass fuels is wood. However, different biomass fuels generate different amount of heat and different amount and type of residuals after burning. Great deviations exist also for different types and qualities of wood. This makes it difficult to control a burning or combustion process effectively.

Thus, it is often of great importance to be able to estimate the heating value of a biological material. For example in bio energy systems, including burning systems, it is of great importance to estimate the heating value of the material fed to the bio energy system, in order to control the burning process more precisely, and improve its efficiency. The heating value typically varies between different types of biological materials, but also within each type. For example, the same type of biological material may have different moisture content, different ash properties, etc. For example in wood, this may depend on a variety of factors including the type of tree or shrub, the part of the tree or shrub (bark, wood, leaves), etc.

Many suggestions have been proposed during the years to provide estimates of heating value of different materials. For example, U.S. Pat. No. 7,690,268 discloses a method for determining heating value of a flowing material. However, this method can only be used on a single, predetermined material, for which the calorific values are known beforehand. Thus, this method cannot be used when many different materials are used simultaneously. Similarly, the method disclosed in U.S. Pat. No. 3,934,139 is also related to estimation of heating value for one specific material, and also requires determination of the density of the material. The method disclosed in EP 0 718 553 determines the moisture content of a material, and assumes that this is correlated to the heating value. Even though this assumption may be correct for some materials, it is not generally valid, which makes the method difficult to use for systems handling a variety of biological materials. Further, common problems with such known methods are that that the apparatuses are large and expensive, that the methods are relatively tedious and cumbersome to perform, and/or that the results are imprecise and unreliable.

It is therefore a need for a fast and reliable method to estimate the heating value of a biological material, and in particular a method which can be used also when handling a variety of biological materials.

SUMMARY OF THE INVENTION

It is therefore an object of the present invention to provide an improved method and apparatus for estimating the heating value of a biological material, preferably in an automated process, which overcome or at least alleviate the above-discussed problems of the prior art.

This object is achieved by means of the invention as defined in the appended claims.

According to a first aspect of the invention there is provided a method for estimating a heating value of a biological material, comprising:

correlating amounts of radiation transmitted through a number of different reference materials, said radiation being electromagnetic radiation of at least two energy levels, with heating values for said reference materials obtained by calorimeter measurements;

irradiating the biological material with electromagnetic radiation of said at least two different energy levels;

measuring the amount of radiation transmitted through said biological material at said energy levels;

determining, for each energy level, a transmission value through the biological material based on the radiation through said biological material; and determining, based on said determined transmission values and said correlation, an estimate of the heating value of said biological material.

The present invention is based on the surprising realization that the transmission values may be correlated directly to the heating value, without the need to determine the type of biological material used, the moisture content, the ash content, the density etc. It has been found that this correlation is essentially independent of these parameters. With this direct correlation, a greatly simplified and more efficient method for determining heating value is obtained.

The term "heating value" is here used to indicate the efficient energy being obtainable during combustion, in joules or kcal, for unit mass of the biological material. Heating value may also be referred to as calorific value. The method of the present invention may be used either to estimate the gross calorific value, commonly referred to as the high heating value, or the net calorific value, commonly referred to as the low heating value. The difference between the two is that the net calorific value does not include the energy to condense the produced water vapor.

The present invention is particularly useable for estimating the heating value in wood chips, but it may also be used for other forms of wood, as well as for other types of biological material, such other types of biomass fuel, coal, etc. The invention is particularly useful for biological material in a liquid or separated form, and preferably in the form of chips. However, the invention is also useable for other types of biological material.

The method of the present invention makes use of irradiation of two or more different energy levels, and determines the heating value of the material, directly or indirectly, from the measured transmission energy, i.e. the amount of the radiation of each wavelength that is absorbed in the material. Different material types, such as different sort of wood, have different absorption coefficient. However, the inventive system compensates for this in a very effective way by using the correlation to the heating values for the reference materials obtained by calorimeter measurements.

The method/apparatus according to the present invention is very well suited for use in online measurements along conveyor lines where material is transported, in pipe-lines, etc. This is possible, since e.g. the present invention can be used for various and varying heights and forms of the biological material. However, it is also very useable for measuring samples of material arranged in sample containers, e.g. for sample testing in process industries, in the field measurements, etc. The present invention may be used in fully or partly automated procedures, and requires no, or very limited, operator interaction.

The reference measurements to obtain the correlation is preferably assembled by measuring transmission of electromagnetic radiation of at least two different energy levels through a plurality of different material types, and by measuring the heating value of said materials by means of a conventional method. The material types may e.g. be different sorts of wood, such as birch, spruce, pine, oak, and alder, and also coal and other biofuels. Since the correlation needs only be established during the initialization, and can then be reused repeatedly, there is no particular need for speedy processes during these reference measurements.

Due to the efficient estimation of the heating value, it is possible to control the burning/combustion process in relation to the heating value, in order to obtain a more effective burning/combustion.

The present invention may be used in fully or partly automated procedures, and requires no, or very limited, operator interaction. The sending of information related to the heating value to a control system and the use of said information for the control of the subsequent process may also be automated. When used in an in-line system, the subsequent process can hereby be controlled in real-time based on said information. However, it is also possible to store the information for later use in association with the specific sample or batch of biological material.

The calorimeter measurement for determining the heating values for said reference materials is preferably an adiabatic bomb calorimeter measurement. Most preferably, the adiabatic bomb calorimeter measurement is made in accordance with international standard ISO 1928:1995.

The determination of the estimated heating value preferably comprises the steps of:

determining a quotient between transmission estimates based on said transmission values of two of said at least two energy levels, for each combination of said at least two energy levels;

multiplying each quotient with a coefficient for each quotient; and adding said quotients multiplied by said coefficients, wherein said coefficients are determined by said correlation.

Thus, the heating value is calculated based on the quotient between two or more measurements of different energy levels, as:

$$W = a*K1 + b*K2 + c*K3 + \ldots$$

K is here the quotient between measurements at different energy levels.

Hereby, if two energy levels are used, one K is obtained. If three energy levels are used, three K:s are obtained. If four energy levels are used, six K:s are obtained, etc. If three energy levels are used, the three K:s would be: K1=R1/R2, K2=R2/R3 and K3=R1/R3.

Thus, for only two energy levels, the heating value may be estimated as $W=a*K1$, and if three energy levels are used, as $W=a*K1+b*K2+c*K3$, and if four energy levels are used, as $W=a*K1+b*K2+c*K3+d*K4+e*K5+f*K6$.

The coefficients, denominated a-f above, are determined in the above-discussed correlation, based on the reference measurements. The correlation between heating value and the transmission values is surprisingly good even if only two energy levels are used, but is improved even further if three or more energy levels are used. Preferably, three distinct energy levels are used.

Preferably, the transmission estimates in said quotients are logarithmic quotients of a calibrated reference values for the transmission at the energy level and the transmission values through the biological material at the same energy level. Thus, $Rx=Ln(N0x/Nx)$. Most preferably, the quotients between said transmission estimates are K-values, said K-values being calculated as:

$$K_{AB} = \frac{\ln(N_{0A}/N_A)}{\ln(N_{0B}/N_B)}$$

wherein N0A, N0B are the calibrated reference values for the transmission at the two energy levels A and B, and NA, NB are the transmission values through the biological material at said energy levels.

It has been found by the present inventors that the correlation between the K-value(s) and the heating value(s) is relatively linear for many types of biological material, in particular for many sorts of wood, and accordingly, relatively few specific values from the reference measurements can still be used to provide accurate estimations of a broad range of heating values in the sample material.

The amount of radiation transmitted through the sample of the biological material at the two energy levels is preferably determined in relation to a calibration reference value. The calibration reference value can e.g. be determined by measurement of the transmission of radiation through a reference material of a predetermined thickness, which is preferably made immediately before and/or after the each measurement through the biological material, the reference material e.g. being aluminum. Hereby, it is ensured that adequate calibration is always at hand.

The biological material is preferably transported on a conveyor line, wherein the biological material is irradiated with electromagnetic radiation of at least two different energy levels in a plane substantially perpendicular to a direction of advancement of said conveyor line. Hereby, the amount of radiation transmitted through said biological material at said two energy levels is preferably determined for a plurality of radiation paths penetrating said biological material in the plane substantially perpendicular to the direction of advancement of said conveyor line.

The at least two different energy levels are both preferably of X-ray radiation wavelengths. Further, the radiation of both said energy levels are preferably emitted from a single radiation source operating in the energy range 20-150 kVp. Here, kVp (Peak kilovoltage) denotes the maximum voltage applied across an X-ray tube. It determines the kinetic energy of the electrons accelerated in the X-ray tube and the peak energy of the X-ray emission spectrum. The actual voltage across the tube may fluctuate.

The irradiation of the sample of the biological material with electromagnetic radiation of at least two different energy levels preferably comprises a first irradiation with a first energy level, and a subsequent second irradiation with a second energy level. Alternatively, the radiation source may comprise two or several separate juxtaposed radiation tubes which radiate either simultaneously or sequentially. Preferably, the different wavelength radiation traverses the material to be measured along essentially the same path.

According to a second aspect of the invention, there is provided an apparatus for estimating a heating value of a biological material, comprising the steps of:

a radiation source for irradiation of a biological material with electromagnetic radiation of at least two different energy levels;

a detector for receiving electromagnetic radiation transmitted through said biological material, for determination, for each energy level, a transmission value through the biological material;

a controller arranged to correlate amounts of radiation transmitted through a number of different reference materials, said radiation being electromagnetic radiation of at least two energy levels, with heating values for said reference materials obtained by calorimeter measurements, and to determining, based on said determined transmission values and said correlation, an estimate of the heating value of said biological material.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein:

FIG. 2a-b schematically illustrates an embodiment of the invention where the material to be measured is arranged in a sample container, wherein FIG. 2a is a schematic top view of the measurement apparatus, and FIG. 2b is a simplified side view of the apparatus of FIG. 2a, where some of the components of the apparatus as shown in FIG. 2a have been excluded for increased clarity.

DETAILED DESCRIPTION OF PREFERRED EMBODIMENTS

Figure 1:
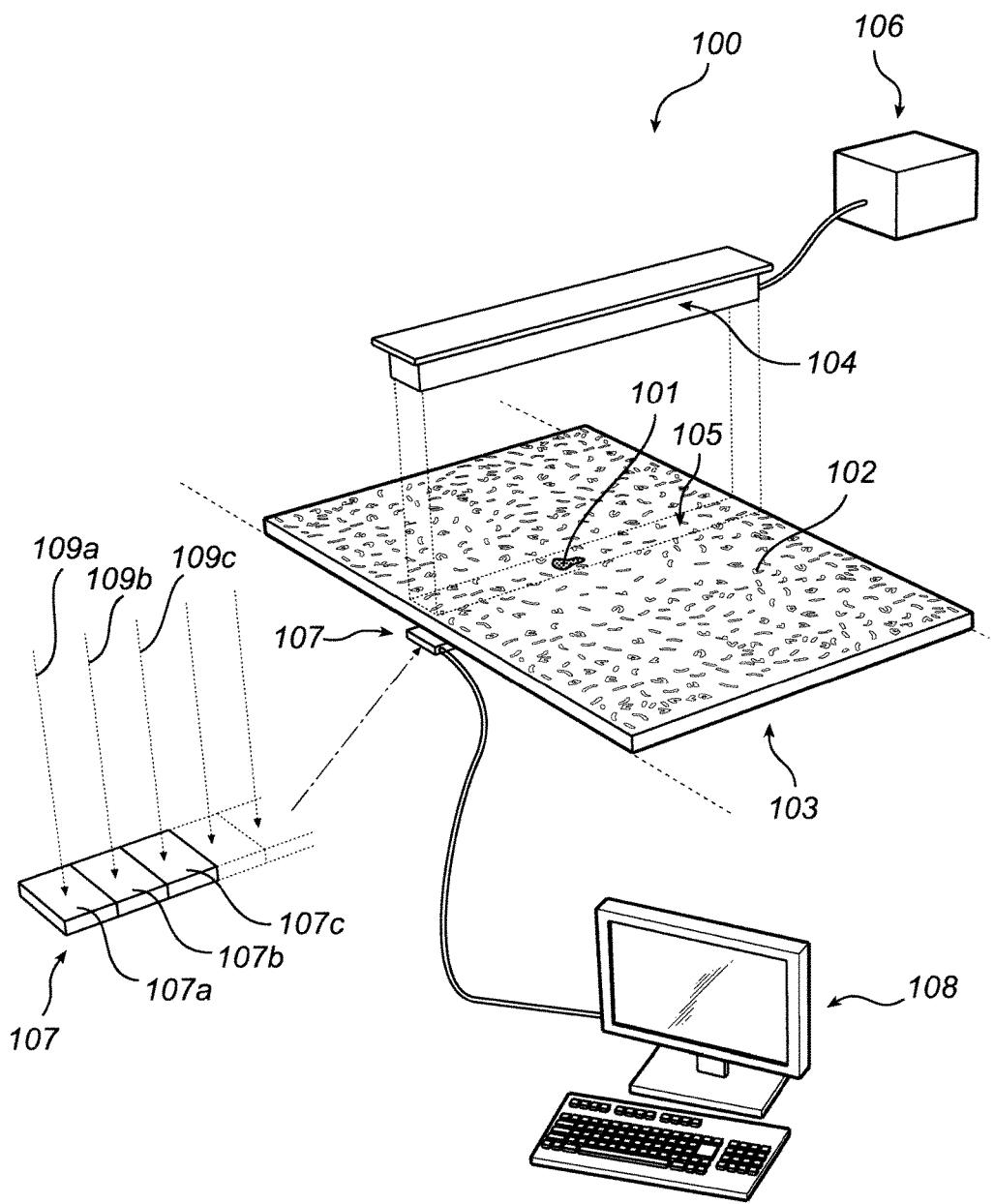
FIG. 1 schematically illustrates a measurement device for estimating a heating value in a biological material transported on a conveyor line.

FIG. 1 schematically illustrates an embodiment of a measurement device 100 for estimating a heating value of a biological material 102 transported on a conveyor line 103. The biological material 102 may typically be wood chips, or other biomass fuels.

If the height and properties of the material varies, it is preferred to scan essentially all of the material moved past the measurement device. If there is no significant variation in height and material properties over time, it may suffice to measure in a single point or target area.

In order to scan essentially all of the material, the measurement device comprises a radiation source 104 adapted to irradiate a target area 105 that spans across the width of the conveyor line. The radiation source 104 is adapted to provide radiation of at least two different energy levels/wavelengths. Preferably, the radiation source is an X-ray tube for provision of X-ray radiation of two or more different wavelengths. Preferably, the X-ray tube operates in the range 20-150 kVp. The output radiation from the radiation source is preferably directed towards the target area through a collimator and a lens (not shown). The radiation source 104 is controlled by means of a controller 106.

Alternatively, the radiation source 104 may comprise two or several separate juxtaposed radiation tubes, wherein the juxtaposed radiation sources radiate the different wavelengths either simultaneously or sequentially. However, preferably the different wavelength radiation traverses the material to be measured along essentially the same path. When radiation of two (or more) wavelengths is emitted simultaneously from the radiation source the intensity of the two signals should preferably be measured individually. This may be effected directly by making provisions such that certain portions of the detector by filtration only measure radiation having a certain energy level while others measure other energy levels. It may also be effected by subsequent treatment of signals, allowing superimposed signals to be separated.

On the opposite side of the target area 105, a detector 107 is arranged to receive radiation transmitted through material located in the target area 105. The detector is preferably a semiconductor detector comprising a linear array of semiconductor detector areas 107a-c distributed across the width of the conveyor line. The number of detector areas may vary due to the expected variations of ash content in the material, etc. The detector 107 is connected to a control unit 108 with a processor, e.g. an ordinary personal computer. The control unit receives detection data from the detector through a suitable interface, such as through a USB port.

In operation, the radiation source 104 irradiates the material in the target area 105 with electromagnetic radiation of at least two different energy levels. This may be achieved by sequentially irradiating the material with radiation of a first wavelength, and radiation of a second wavelength, i.e. the radiation source initially emits rays having one wavelength and then, by altering the voltage across the radiation tube, a different wavelength.

For each energy level, the amount of radiation transmitted through the material located in the target area 105 is measured on the opposite side of the target area 105 by the detector areas 107a-c of the detector, wherein each detector area 107a-c receives radiation that has penetrated the material 102 along a different radiation path 109a-c.

In order to get a reference value for calibration, it is preferred to measure a calibration material. This can be achieved, for example, by measuring without any biological material present. Thus, in this case, a calibration measurement is obtained with air as a calibration material. Alternatively, the biological material may be replaced with a calibration material with known properties, such as aluminum. The calibration measurements may be obtained before measuring of the biological material, during initialization, or repeatedly during the process. Alternatively, calibration measurements may be obtained by relocating the radiation source 104 and the detector 107 to a location next to the conveyor line such that the radiation passes through air only on its way from the radiation source to the detector. It is also possible to use additional radiation sources and detectors situated on one or both sides of the conveyor belt.

Based on these calibration measurements, calibration values are determined as:

$$N_{01,02} = N_{Air1,2} \exp(\mu x)$$

where $N_{01}$ and $N_{02}$ are the calibration values for energy level 1 and 2, respectively, $N_{Air1}$ and $N_{Air2}$ are the detected transmission values after passage through the known distance of air, μ is the known attenuation coefficient for air (cm$^{-1}$) and x is the known distance of air (cm) that separates the radiation source and the detector.

A K-value for the material is determined for the radiation received by each detector area 107a-c. The K-value is calculated as:

$$K = \frac{\ln(N_{01}/N_1)}{\ln(N_{02}/N_2)}$$

wherein $N_{01}$, $N_{02}$ are the calibrated reference values for the transmission at the two energy levels and $N_1$, $N_2$ are the transmission values through the biological material at the energy levels.

A correlation between heating values and the amounts of radiation transmitted through the biological material is then determined. This is determined based on reference measurements of a number of different reference materials.

The reference measurements are preferably made as calorimeter measurement of standard type, and preferably an adiabatic bomb calorimeter measurement is used. Most preferably, the adiabatic bomb calorimeter measurement is made in accordance with international standard ISO 1928: 1995.

The correlation between the heating values of the reference measurements and the transmission values is preferably made by correlation to the above-discussed K-values. Preferably, the heating value is calculated based on the quotient between two or more measurements of different energy levels, as:

$$W = a*K1 + b*K2 + c*K3 + \ldots$$

where K is the quotients between each and every combination of measurements at different energy levels. Hereby, if two energy levels are used, one K is obtained. If three energy levels are used, three K:s are obtained. If four energy levels are used, six K:s are obtained, etc. If three energy levels are used, the three K:s would be: K1=R1/R2, K2=R2/R3 and K3=R1/R3. Thus, for only two energy levels, the heating value may be estimated as W=a*K1, and if three energy levels are used, as W=a*K1+b*K2+c*K3, and if four energy levels are used, as W=a*K1+b*K2+c*K3+d*K4+e*K5+f*K6. The coefficients, denominated a-f above, are determined and optimized mathematically to provide a correlation between the reference measurements and the heat energy as estimated based on the transmission measurements. Thus, the K-values may be used in a linear or polynomial representation of the correspondence between the K-value and the heating value, and this function may then be used for an estimate of the heating value based on the measured and calculated K-values of the sample material.

Figure 3:
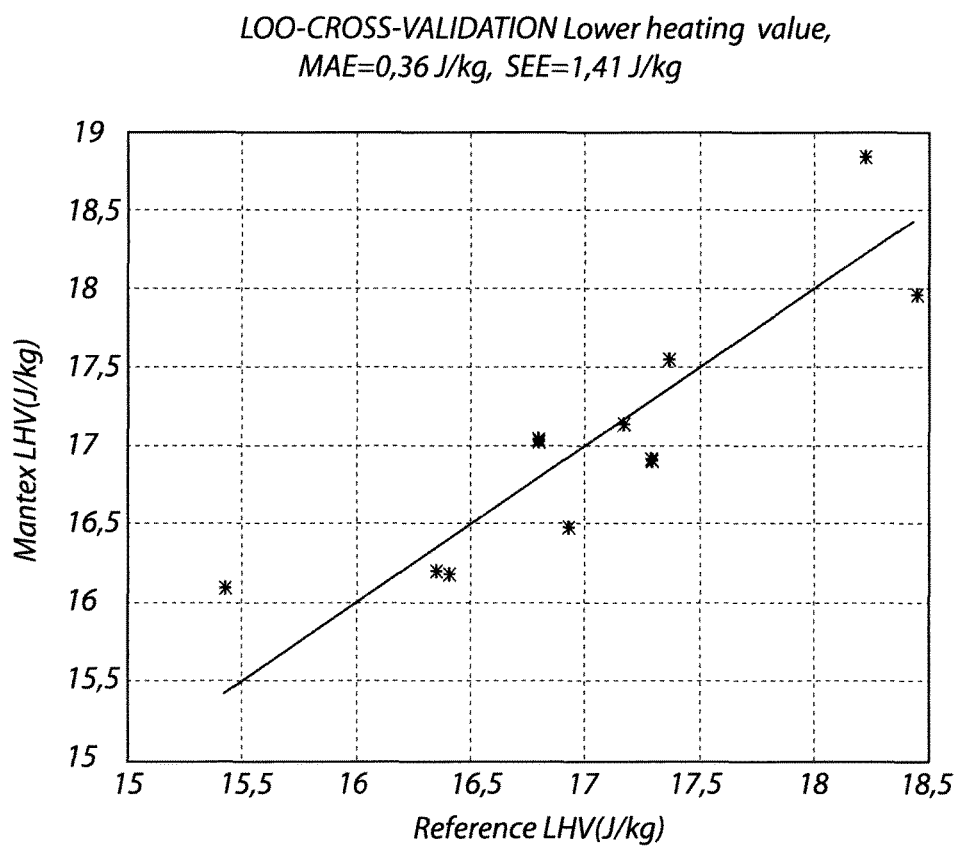
FIG. 3 is a graph showing the correlation between heating values estimated based on K-values, and heating values measured in an adiabatic bomb calorimeter, for a number of different biological materials.

It has been found by the present inventors that a good approximation of the heating values, and a good correlation between the reference measurements and the estimation based on the transmission measurements, can be achieved. In FIG. 3, a graph is provided showing heating values estimated based on K-values on one axis, and heating values measured by reference measurements in an adiabatic bomb calorimeter on the other axis, for a number of different biological materials. The transmission measurements were here made with three different energy levels, but already with two energy levels, a relatively good correlation can be achieved. As can be determined from FIG. 3, the transmission measurements enables the calculation of a good approximation of the real heating value, which enables fast and cost-efficient estimation of the heating values, which can e.g. be used in continuous in-line measurements and the like.

The estimated heating values may be used by the control unit 108, or by other control units, to control e.g. a burning or combustion process effectively.

Figure 2A:
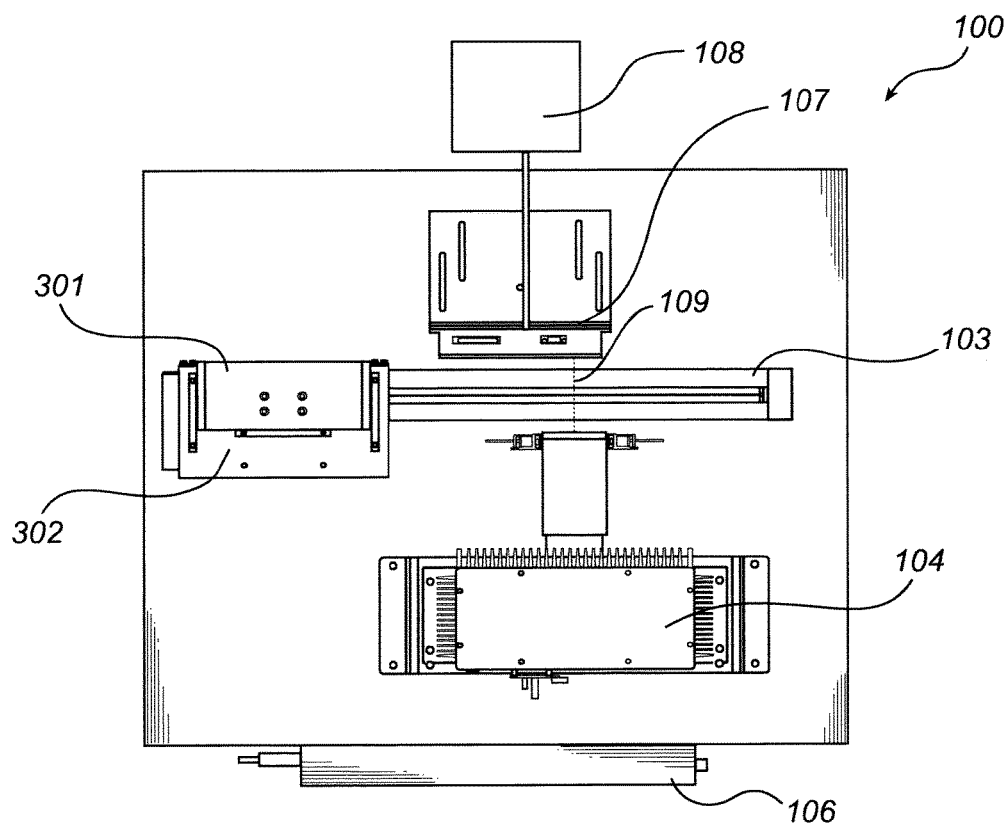
Figure 2B:
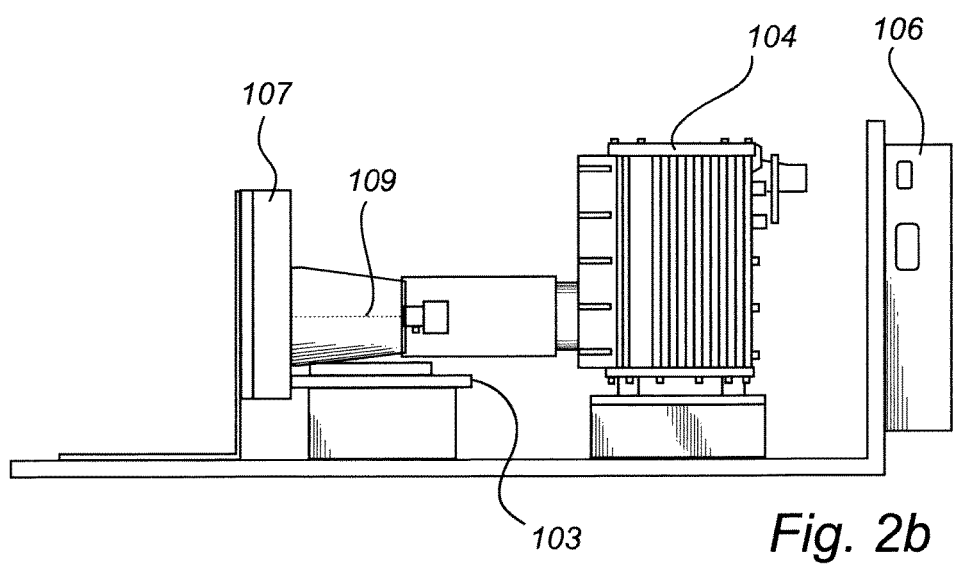

FIG. 2a-b schematically illustrates an alternative embodiment of a measurement device according the invention. The measurement device 100 comprises a radiation source 104 for irradiating a target area with at least two energy levels/wavelengths. Preferably, the radiation source is an X-ray tube for provision of X-ray radiation of two or more different wavelengths. Preferably, the X-ray tube operates in the range 20-150 kVp. The output radiation from the radiation source is preferably directed towards a target area through a collimator and a lens. The radiation source is controlled by means of a controller 106. A detector 107 is arranged on the opposite side of the target area. The detector is connected to a control unit 108 that receives detection data from the detector. In this embodiment, the material to be measured is arranged in a sample container 301. The sample container is then arranged on a carrier 302, which is movable in such a way that the sample container is moved through the target area, and thus through the radiation path 109. The carrier may e.g. be moved by means of a conveyor 103. However, other means for moving the carrier are also feasible, such as linear motors, screw arrangements, rail arrangements and the like.

During operation, the sample container is moved through the target area such that preferably all of the material in the sample container is scanned. At the first passage, the material sample is irradiated with radiation of a first wavelength, and in the second passage, during the return movement, with radiation of a second wavelength. In order to get a reference value for calibration, it is preferred to measure a calibration material, preferably a predetermined amount of aluminum, at the beginning and end of the passage of the sample container.

Based on these calibration measurements, calibration reference values may be determined in the same way as discussed above, and further, K-value and heating values for the biological material may be calculated as discussed above.

Specific embodiments of the invention have now been described. However, several alternatives are possible, as would be apparent for someone skilled in the art. For example, the radiation need not be X-ray, but other types of electromagnetic radiation may also be used.

Further, the radiation paths through the material may be arranged in various ways. For example, the paths may travel essentially along a single line, between a radiation source and a detector, or several detectors arranged overlapping or close to each other. However, the radiation paths may also be arranged along parallel lines, to form a "curtain" like measurement zone. It is also possible to use a plurality of non-parallel paths, e.g. extending from a single radiation source to a plurality of spread out detectors, to form a "fan shaped" measurement zone. Similarly, it would also be possible to use a plurality of separated radiation emerging points, and a single detection point, or the like. Many other types of geometries for the paths are also feasible.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. A method for estimating a heating value of a biological material, comprising:
    correlating amounts of radiation transmitted through a number of different reference materials, said radiation being X-ray radiation of at least two energy levels, with heating values for said reference materials obtained by calorimeter measurements;
    irradiating the biological material with X-ray radiation of said at least two different energy levels;
    measuring the amount of radiation transmitted through said biological material at said energy levels;
    determining, for each energy level, a transmission value through the biological material based on the radiation through said biological material; and
    determining, based on said determined transmission values and said correlation, an estimate of the heating value of said biological material.

2. The method of claim 1, wherein calorimeter measurement for determining the heating values for said reference materials is an adiabatic bomb calorimeter measurement.

3. The method of claim 2, wherein the adiabatic bomb calorimeter measurement is made in accordance with international standard ISO 1928:1995.

4. The method of claim 1, wherein the determination of the estimated heating value comprises the steps of:
    determining a quotient between transmission estimates based on said transmission values of two of said at least two energy levels, for each combination of said at least two energy levels;
    multiplying each quotient with a coefficient for each quotient; and
    adding said quotients multiplied by said coefficients, wherein said coefficients are determined by said correlation.

5. The method of claim 4, wherein the transmission estimates in said quotients are logarithmic quotients of a calibrated reference values for the transmission at the energy level and the transmission values through the biological material at the same energy level.

6. The method of claim 5, wherein the quotients between said transmission estimates are K-values, said K-values being calculated as:

$$K_{AB} = \frac{\ln(N_{0A}/N_A)}{\ln(N_{0B}/N_B)}$$

wherein $N_{0A}$, $N_{0B}$ are the calibrated reference values for the transmission at the two energy levels A and B, and $N_A$, $N_B$ are the transmission values through the biological material at said energy levels.

7. The method of claim 6, wherein the calibration reference value is determined by measurement of the transmission of radiation through a reference material, said calibration measurement preferably being made immediately before and/or after the each measurement through the biological material, the reference material preferably being aluminum.

8. The method of 1, wherein the biological material is transported on a conveyor line, wherein the biological material is irradiated with X-ray radiation of at least two different energy levels in a plane substantially perpendicular to a direction of advancement of said conveyor line.

9. The method of claim 8, wherein the amount of radiation transmitted through said biological material at said two energy levels is determined for a plurality of radiation paths penetrating said biological material in the plane substantially perpendicular to the direction of advancement of said conveyor line.

10. The method of claim 1, wherein the radiation of both said energy levels are emitted from a single radiation source operating in the energy range 20- 150 kVp.

11. The method of claim 1, wherein the heating value is a lower heating value.

12. The method of claim 1, wherein X-ray radiation of at least three energy levels is used.

13. The method of claim 1, wherein the irradiation of the biological material with X-ray radiation of at least two different energy levels comprises a first irradiation with a first energy level, and a subsequent second irradiation with a second energy level.

14. The method of claim 1, wherein the biological material is transported on a conveyor line, wherein the biological material is irradiated with X-ray radiation of at least two different energy levels in a plane substantially perpendicular to a direction of advancement of said conveyor line, and wherein the radiation source is adapted to irradiate a target area that spans across the width of the conveyor line.

15. The method of claim 1, wherein the radiation transmitted through the biological material is detected by a detector arranged on the opposite side of the biological material than the X-ray radiation source.

16. The method of claim 1, wherein correlating amounts of radiation transmitted through a number of different reference materials with heating values for said reference materials obtained by calorimeter measurements is conducted without determining the type of biological material used and the moisture content of the reference material.

17. An apparatus for estimating a heating value of a biological material, comprising the steps of:
    a radiation source for irradiation of a biological material with X-ray radiation of at least two different energy levels;
    a detector for receiving X-ray radiation transmitted through said biological material, for determination, for each energy level, a transmission value through the biological material;
    a controller arranged to correlate amounts of radiation transmitted through a number of different reference materials, said radiation being X-ray radiation of at least two energy levels, with heating values for said reference materials obtained by calorimeter measurements, and to determine, based on said determined transmission values and said correlation, an estimate of the heating value of said biological material.

18. A method for estimating a heating value of a biological material, comprising:
    correlating amounts of radiation transmitted through a number of different reference materials, said radiation being X-ray radiation of at least two energy levels, with heating values for said reference materials obtained by calorimeter measurements without determining the type of reference material and the moisture content of the reference material;

transporting the biological material on a conveyor line;

irradiating through the biological material with X-ray radiation of said at least two different energy levels in a plane substantially perpendicular to a direction of advancement of the conveyer line;

measuring the amount of radiation transmitted through said biological material at said energy levels;

determining, for each energy level, a transmission value through the biological material based on the radiation transmitted through said biological material; and determining, based on said determined transmission values and said correlation, an estimate of the heating value of said biological material.

19. The method of claim 18, the determination of the estimated heating value comprises the steps of:

determining a quotient between transmission estimates based on said transmission values of two of said at least two energy levels, for each combination of said at least two energy levels;

multiplying each quotient with a coefficient for each quotient; and adding said quotients multiplied by said coefficients, wherein said coefficients are determined by said correlation.

20. The method of claim 19, wherein the transmission estimates in said quotients are logarithmic quotients of a calibrated reference values for the transmission at the energy level and the transmission values through the biological material at the same energy level.

21. The method of claim 20, wherein the quotients between said transmission estimates are K-values, said K-values being calculated as:

$$K_{AB}=\ln(N_{OA}/N_A)/\ln(N_{OB}/N_B)$$

wherein $N_{OA}$, $N_{OB}$ are the calibrated reference values for the transmission at the two energy levels A and B, and $N_A$, $N_B$ are the transmission values through the biological material at said energy levels.

22. The method of claim 18, wherein the amount of radiation transmitted through said biological material at said two energy levels is determined for a plurality of radiation paths penetrating said biological material in the plane substantially perpendicular to the direction of advancement of said conveyor line.

23. The method of claim 18, wherein the radiation of both said energy levels are emitted from a single X-ray radiation source operating in the energy range 20-150 kVp.

24. The method of claim 18, wherein X-ray radiation of at least three energy levels is used.

* * * * *